US009103749B2

(12) United States Patent
Nagy

(10) Patent No.: US 9,103,749 B2
(45) Date of Patent: Aug. 11, 2015

(54) BIOLOGICAL SAMPLE COLLECTION APPARATUS

(71) Applicant: Fast Forward Forensics, LLC, Madison, WI (US)

(72) Inventor: Randolph J. Nagy, Madison, WI (US)

(73) Assignee: Fast Forward Forensics, LLC, Madison, WI (US)

( * ) Notice: Subject to any disclaimer, the term of this patent is extended or adjusted under 35 U.S.C. 154(b) by 0 days.

(21) Appl. No.: 13/965,987

(22) Filed: Aug. 13, 2013

(65) Prior Publication Data

US 2014/0105796 A1 Apr. 17, 2014

Related U.S. Application Data

(60) Provisional application No. 61/712,671, filed on Oct. 11, 2012.

(51) Int. Cl.
| | |
|---|---|
| *C12M 1/26* | (2006.01) |
| *C12M 1/28* | (2006.01) |
| *C12M 1/30* | (2006.01) |
| *G01N 1/02* | (2006.01) |
| *B01L 3/00* | (2006.01) |
| *A61B 10/00* | (2006.01) |
| *A61B 10/02* | (2006.01) |
| *G01N 35/10* | (2006.01) |
| *G01N 35/00* | (2006.01) |
| *G01N 15/02* | (2006.01) |

(52) U.S. Cl.
CPC .............. *G01N 1/02* (2013.01); *A61B 10/0096* (2013.01); *B01L 3/00* (2013.01); *A61B 10/0045* (2013.01); *A61B 10/0051* (2013.01); *B01L 3/502* (2013.01); *B01L 3/5635* (2013.01); *B01L 2300/0609* (2013.01); *B01L 2300/0681* (2013.01); *C12M 1/28* (2013.01); *G01N 15/0272* (2013.01); *G01N 2001/028* (2013.01); *G01N 2035/00475* (2013.01); *G01N 2035/1053* (2013.01)

(58) Field of Classification Search
None
See application file for complete search history.

(56) References Cited

U.S. PATENT DOCUMENTS

| | | | |
|---|---|---|---|
| 5,780,305 A | 7/1998 | Chisum | |
| 5,874,045 A | 2/1999 | Chisum | |
| 6,274,304 B1 * | 8/2001 | Buschek et al. | 435/4 |
| 6,383,453 B1 * | 5/2002 | Banauch et al. | 422/550 |
| 6,986,807 B2 * | 1/2006 | Brunk | 96/147 |
| 2004/0082899 A1 * | 4/2004 | Mathias et al. | 604/6.16 |
| 2004/0170536 A1 * | 9/2004 | Daykin | 422/102 |
| 2007/0284300 A1 * | 12/2007 | Bidlingmeyer et al. | 210/450 |
| 2007/0299364 A1 | 12/2007 | Sangha | |
| 2008/0105063 A1 * | 5/2008 | Laugham et al. | 73/863 |

(Continued)

FOREIGN PATENT DOCUMENTS

| | | | | |
|---|---|---|---|---|
| EP | 1748845 | | 8/2009 | |
| WO | WO 2005032377 A1 * | 4/2005 | | A61B 10/00 |

(Continued)

*Primary Examiner* — Jennifer Wecker
(74) *Attorney, Agent, or Firm* — Dunlap Codding, P.C.

(57) ABSTRACT

A testing container is described having a vessel with a first end, a second end, and a sidewall extending between the first end and the second end. The first end forms an opening into the vessel. The sidewall has one or more protrusions extending inwardly therefrom. The one or more protrusions form a gap having a width in a range between 2-4 mm, and the one or more protrusions have sufficient strength to withstand lateral pressure of a swab positioned in the gap relative to the one or more protrusions and to remove a head of the swab.

18 Claims, 7 Drawing Sheets

(56) References Cited

U.S. PATENT DOCUMENTS

| | | |
|---|---|---|
| 2009/0166361 A1* | 7/2009 | Lourenco .................. 220/268 |
| 2009/0215159 A1 | 8/2009 | Kirby |
| 2009/0223983 A1 | 9/2009 | Leary |
| 2010/0111772 A1* | 5/2010 | Hartofelis .................. 422/102 |
| 2012/0196313 A1* | 8/2012 | Williams et al. ................ 435/29 |

FOREIGN PATENT DOCUMENTS

| | | |
|---|---|---|
| WO | 2011106784 | 9/2011 |
| WO | 2012027048 | 3/2012 |

* cited by examiner

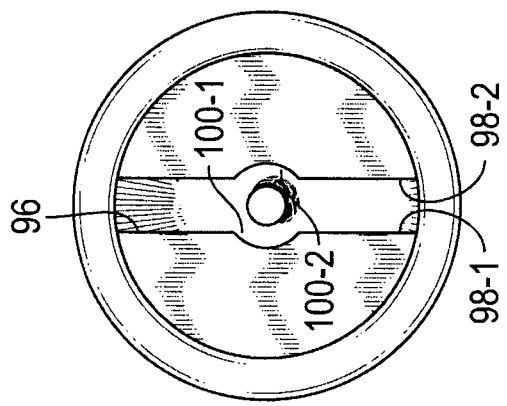
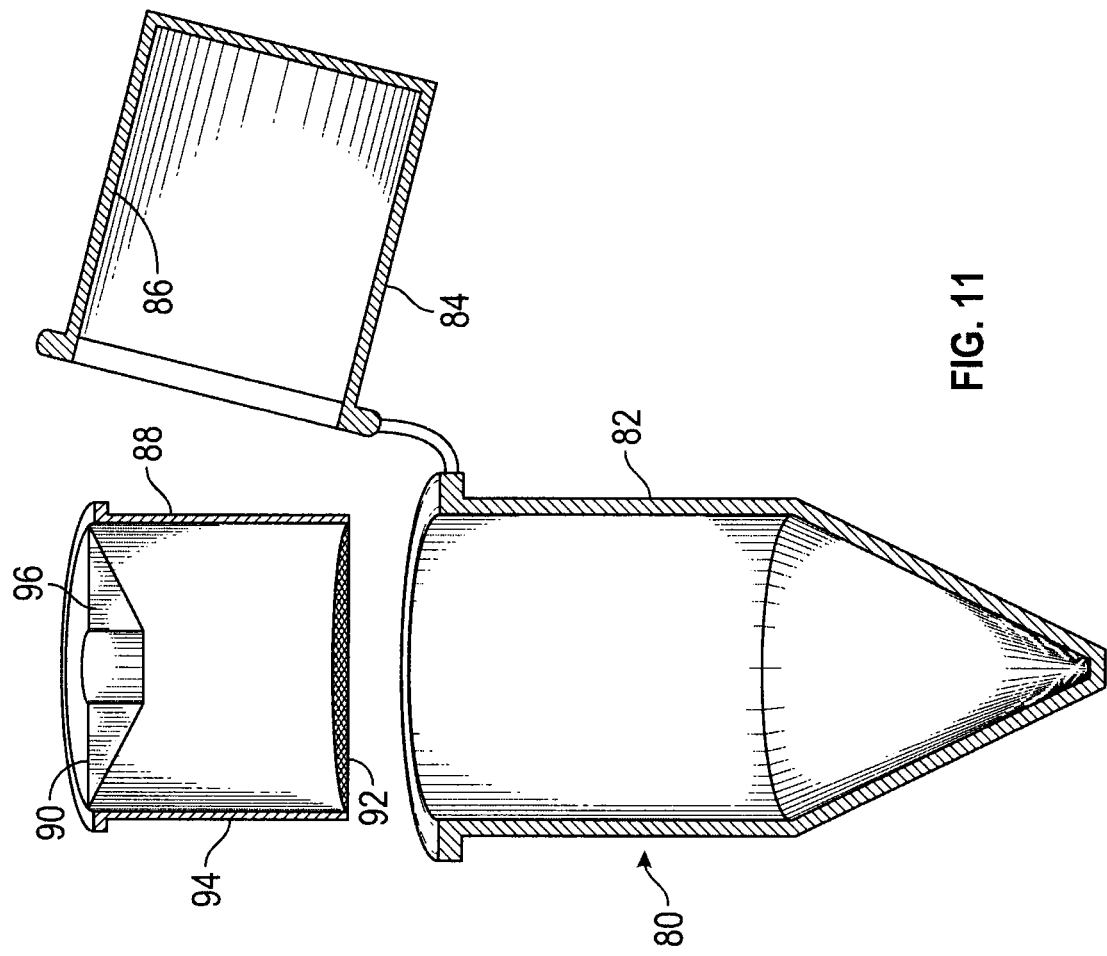

BIOLOGICAL SAMPLE COLLECTION APPARATUS

BACKGROUND

The collection, preservation, and processing of biological samples for DNA testing often requires a number of devices that could introduce DNA contamination and sample mix-up as transfers are made. Biological samples, such as those for forensic DNA analysis, are usually collected from blood, saliva, semen, and other bodily fluids by wiping onto a cotton-tipped swab or a cotton pad. The swabs, pads, or other collection devices are placed into plastic or paper containers or bags for storage, preservation and future analysis. Wet samples could be prone to microbial action and biological degradation if not dried or preserved properly. Cotton swabs or cotton pads may obtain small samples with a limited amount of biological materials which can be contaminated or diminished when the swab or pad comes in contact with the container or bag, or when the swab or pad is transferred to a processing or testing container.

The biological samples are then transferred to microtiter plates or tubes like microfuge tubes for testing or processing. Microfuge tubes are small plastic tubes capable of holding between 0.4-2.0 ml of liquid and are constructed to be placed into racks for automated manipulation and withstand the forces exerted by a centrifuge during centrifugation. Biological samples that may have dried in the previous container may be removed from the previous container, inserted into the microfuge tubes, and combined with a solution to separate DNA, for instance. The microfuge tubes usually have caps sized and shaped to protect and cover the tube opening, while maintaining the inside of the tube in an aseptic condition. The caps are usually attached by a flexible hinge and are closed and secured by press fit. Closing the cap often causes an annular sealing portion of the underside of the cap to be pushed downward into the tube. The caps are secured against accidental opening by a number of means which vary in effectiveness, including friction, integrated lid catches, or separate lid clamps. The caps are often provided with an unsealing portion opposite the cap hinge extending horizontally beyond the outer diameter of the tube's cap flange to provide a standard lifting tab. A thumb, thumbnail, or opener device may be used to lift upward on the lifting tab, but may lead to contamination of the sample held within the microfuge tube. Even the use of surgical gloves may not prevent cross-contamination between successively opened microfuge tubes. Container opener tools may reduce incidence of contamination however may not preclude contamination.

Biological samples that are not immediately processed and tested may be stored in the collection container for indefinite periods of time, in which case, the biological samples will benefit from drying or other preservation techniques to prevent degradation of the sample. Traditionally sample drying has been allowed to occur naturally, or aided by the use of protected holes in the cap of a container whereby air is allowed to circulate while limiting potential contact between the sample and contaminants. Drying or preservation agents, such as desiccants, may be used. However drying or preservation agents present contamination problems where the agent is placed in the same container as the biological sample.

There is a need for a container which may serve as the collection, processing, and testing container for biological samples, preventing the possibility of contamination of samples through transfer between containers. Further, there is a need for a container which aids in drying and preservation of biological samples without the potential contamination effects of exposing the biological sample to outside airflow or contamination by contact with a drying or preservation agent.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one version, the present disclosure is directed to a testing container having a vessel and a cap. The vessel may be provided with a first end, a second end, and a sidewall extending between the first end and the second end. The first end of the testing container may form an opening into the vessel. The sidewall is provided with one or more protrusions extending inwardly therefrom. The cap has a first end, a second end, and a desiccant chamber. The cap is configured to fill and seal the opening of the vessel. The second end of the cap is provided with a semi-permeable barrier configured to allow air and moisture circulation between the vessel and the desiccant chamber. The desiccant chamber is configured to house a desiccant.

In another version, the present disclosure describes a testing container with a vessel and a cap. The vessel has a first end, a second end, and a sidewall extending between the first end and the second end. The first end may form an opening into the vessel. The second end may form a closed end of the vessel opposite the first end. The cap has a first end, a second end, and a desiccant chamber. The cap is configured to fill and seal the opening of the vessel, the second end of the cap has a semi-permeable barrier configured to allow air and moisture circulation between the vessel and the desiccant chamber when the second end is positioned within the vessel. The desiccant chamber is configured to house a desiccant.

In another version, the present disclosure describes an insert vessel. The insert vessel has a vessel with a first end, a second end, and a sidewall extending between the first end and the second end. The first end may form an opening into the vessel. The second end may be permeable to a sample fluid passing through the insert vessel. The sidewall has one or more protrusions extending inwardly therefrom. The insert vessel is configured to be inserted or secured into a testing container.

BRIEF DESCRIPTION OF THE DRAWINGS

To assist those of ordinary skill in the relevant art in making and using the subject matter hereof, reference is made to the appended drawings, which are not intended to be drawn to scale, and in which like reference numerals are intended to refer to similar elements for consistency. For purposes of clarity, components may be labeled in certain ones of the drawings but not in each drawing.

FIG. 11 is a side elevational view of an embodiment of a testing container and an insert vessel in accordance with the present disclosure;

FIG. 12 is a partial top plan view of the insert vessel of FIG. 11;

DETAILED DESCRIPTION

Figure 2:
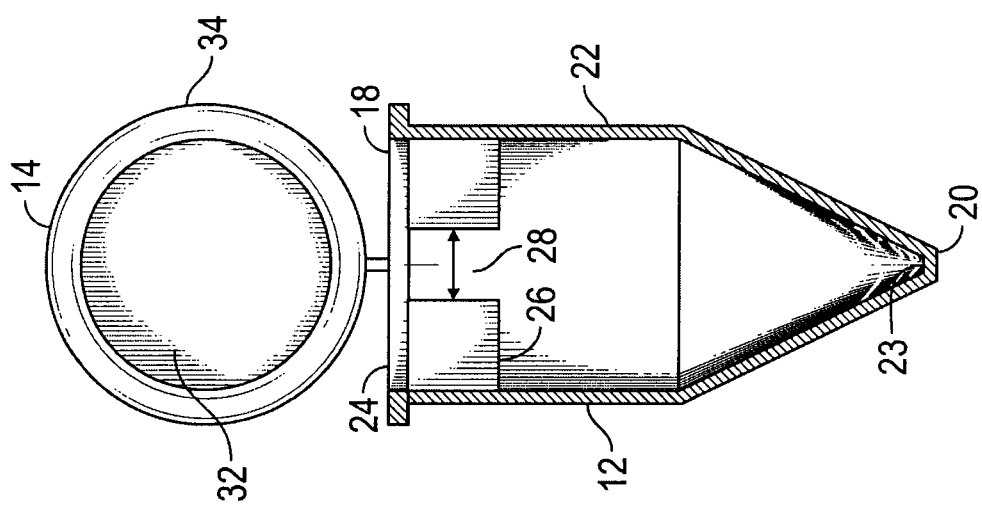
FIG. 2 is a front elevational view of the testing container of FIG. 1.

Specific embodiments of the present disclosure will now be described in detail with reference to the accompanying drawings. It is to be understood that the various embodiments, although different, are not necessarily mutually exclusive. For example, a particular feature, structure, or characteristic described herein in connection with one embodiment may be implemented within other embodiments without departing from the spirit and scope of the present disclosure. Further, in the following detailed description of embodiments of the present disclosure, numerous specific details are set forth in order to provide a more thorough understanding of the present disclosure. However, it will be apparent to one of ordinary skill in the art that the embodiments disclosed herein may be practiced without these specific details. In other instances, well-known features have not been described in detail to avoid unnecessarily complicating the description.

It should also be noted that in the development of any such actual embodiment, numerous decisions specific to circumstance may be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Furthermore, the description and examples are presented solely for the purpose of illustrating the different embodiments, and should not be construed as a limitation to the scope and applicability. While any composition or structure may be described herein as comprising certain materials, it should be understood that the composition could optionally comprise two or more different materials. In addition, the composition or structure can also comprise some components other than the ones already cited.

It should also be understood that throughout this specification, when a range is described as being useful, or suitable, or the like, it is intended that any value within the range, including the end points, is to be considered as having been stated. Furthermore, each numerical value should be read once as modified by the term "about" (unless already expressly so modified) and then read again as not to be so modified unless otherwise stated in context. For example, "a range of from 1 to 10" is to be read as indicating each possible number along the continuum between about 1 and about 10. In other words, when a certain range is expressed, even if a few specific data points are explicitly identified or referred to within the range, or even when no data points are referred to within the range, it is to be understood that the inventors appreciate and understand that any data points within the range are to be considered to have been specified, and that the inventors have possession of the entire range and points within the range.

Figure 1:
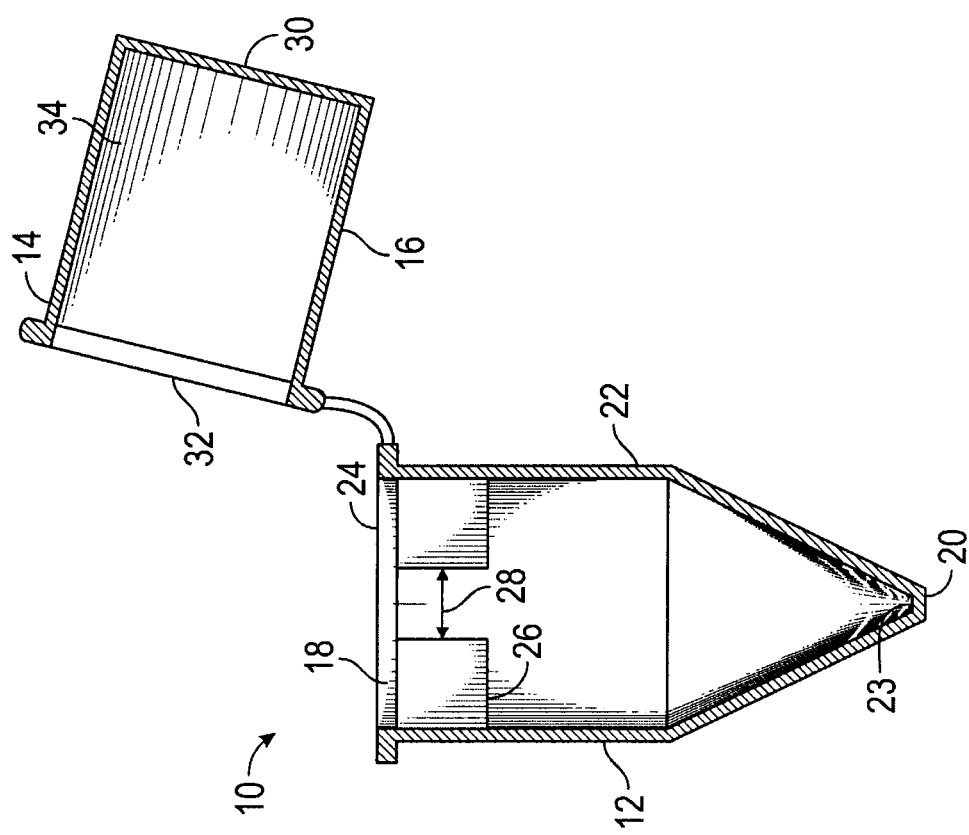
FIG. 1 is a side elevational view of a testing container in accordance with the present disclosure.

Referring now to FIGS. 1 and 2, therein shown is a testing container 10. The testing container 10 is provided with a vessel 12, a cap 14, and a desiccant chamber 16 formed within the cap 14. The testing container 10 may be formed from polyethylene, polyallomer, polypropylene, glass, or other suitable materials. In one embodiment, the testing container 10 may be formed using, for example, injection molding, and may be formed such that the vessel 12, cap 14, and desiccant chamber 16 are of a single piece construction. In another embodiment, the vessel 12 may be formed separate from the cap 14 and the desiccant chamber 16 such that the cap 14 and the desiccant chamber 16 may be secured to the vessel 12. In one embodiment, the testing container 10 may be configured to a standard size of a microfuge tube such that the testing container 10 may be inserted, with the cap 14 opened or closed, within a microfuge or liquid handling robot for automated processing.

The vessel 12 is provided with a first end 18, a second end 20 opposite the first end 18, and a sidewall 22 extending between the first end 18 and the second end 20. The first end 18 forms an opening 24 into the vessel 12. The sidewall 22 is provided with one or more protrusions 26 extending inwardly therefrom. The one or more protrusions 26 may be used to break a shaft of a swab containing a sample as discussed above. The sidewall 22 may be tapered proximate to the second end 20 with the second end 20 forming a closed end 23 and a rounded bottom of the vessel 12. It will be understood that the sidewall 22 may be provided with a taper or without taper and the second end 20 may be rounded, flat, or pointed and remain within the scope of the present disclosure and the inventive concepts disclosed herein. The vessel 12 may be configured for insertion into a microfuge or other centrifuge or liquid handling robot for automated processing. In one embodiment, the vessel 12 may be sized to contain between 1.2-2.0 mL of fluid, for example. In one embodiment, the vessel may be between 35-45 mm in height, and have an internal diameter of between 5-11 mm, for example. It will be understood, however, that the vessel 12 may be of varying height and diameter without departing from the function and the spirit of the inventive concepts of the present disclosure. The one or more protrusions 26 may be formed from polyethylene, polyallomer, polypropylene, glass, or other suitable materials and formed through the same process as the vessel 12, such that the one or more protrusions 26 form a part of the vessel 12. The one or more protrusions 26 may also be formed independent of the sidewall 22 and connected thereto such that the one or more protrusions 26 extend inwardly from the sidewall 22.

Figure 3:
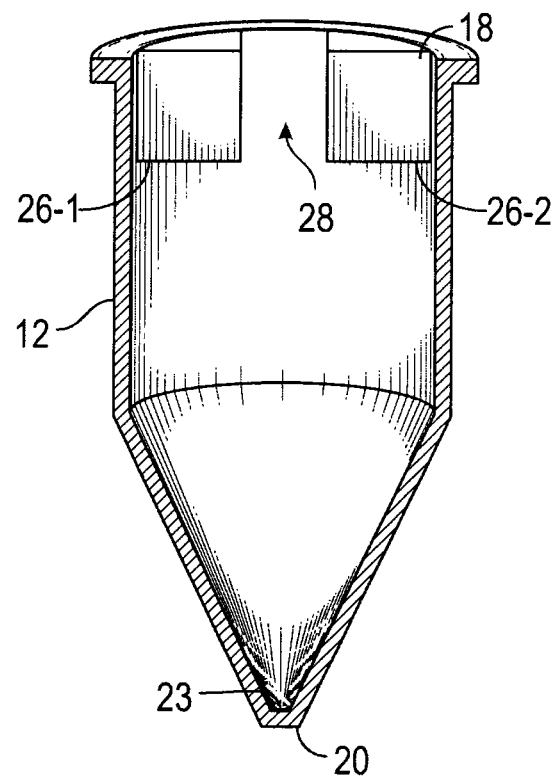
FIG. 3 is a partial side elevational view of the testing container of FIG. 1 with a cap removed.
Figure 4:
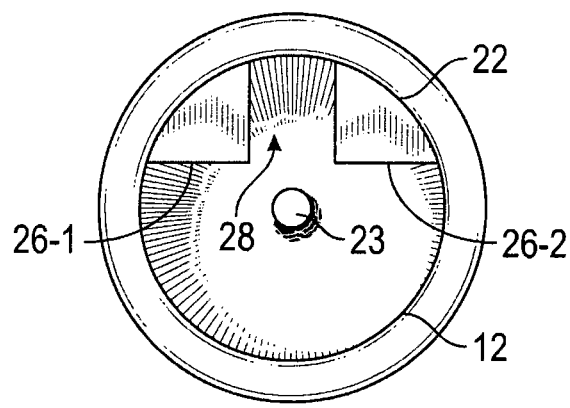
FIG. 4 is a partial top plan view of the testing container of FIG. 1 with the cap removed.

In the embodiment shown in FIGS. 3 and 4, a first protrusion 26-1 and a second protrusion 26-2 are illustrated, as the one or more protrusion 26, extending inwardly approximately one third of the internal diameter of the vessel 12 on opposing sides of the vessel 12 with a gap 28 having a width extending approximately one third of the internal diameter of the vessel 12, for example between about 2-4 mm, between the first and second protrusions 26-1 and 26-2. In this embodiment, the first and second protrusions 26-1 and 26-2 extend proximate to the first end 18 of the vessel toward the second end 20 of the vessel 12 approximately 5-7 mm along the interior of the sidewall 22. It will be understood, however, that the one or more protrusion 26 may be of varying dimensions so long as the protrusions 26-1 and 26-2 may aid a user to break the shaft of the swab and thereby remove a head of the swab, as described below.

Referring again to FIGS. 1 and 2, the cap 14 has a first end 30, a second end 32, a sidewall 34 extending between the first end 30 and the second end 32, and the desiccant chamber 16 formed therein and defined by the sidewall 34. The first end 30 and the sidewall 34 may create a vessel within the cap defining the desiccant chamber 16. The second end 32 of the cap 14 may be formed of a material configured as an air/moisture barrier, a semi-permeable barrier or semi-permeable membrane. For example, the material may be paper, or a polymeric material in a mesh configuration, a slotted configuration, or any other suitable material or configuration which may prevent a desiccant stored within the desiccant chamber 16 from contacting contents of the vessel 12 or entering the vessel 12. When the cap 14 is closed on the vessel 12 and secured to seal the contents of the vessel 12, the second end 32 of the cap 14 may allow air and moisture circulation between the vessel 12 and the desiccant chamber 16. The circulation of air and moisture between the vessel 12 and the desiccant chamber 16 may allow a desiccant within the desiccant chamber 16 to absorb moisture within the vessel 12 and the desiccant chamber 16. In some embodiments, the cap 14 may be provided without the desiccant chamber 16. In this embodiment, the second end 32 may employ a semi-permeable membrane may to allow air/moisture circulation between the vessel 12 and an environment outside of the vessel 12 while retaining a sample stored within the vessel 12 and preventing contamination of the sample. In other embodiments without the desiccant chamber 16, the cap 14 may be provided without the semi-permeable membrane to prevent communication between the vessel 12 and the environment outside of the vessel 12.

The cap 14 may be formed from polyethylene, polyallomer, polypropylene, glass, or other suitable materials, for example. In one embodiment, the cap 14 may be provided integral to the vessel 12 and made during the same process as the vessel 12. In another embodiment, the cap 14 may be provided as a separate piece securable proximate to the first end 18 of the vessel 12. The cap 14 may have an internal diameter of 5-11 mm, for example, to correspond to the internal diameter of the vessel 12. The cap 14 may be between 6-13 mm in height between the first and second ends 30 and 32. It will be understood, however, that the cap 14 may be of varying heights and diameters without departing from the function and the spirit of the inventive concepts of the present disclosure. In some embodiments where the second end 32 is a semi-permeable barrier or membrane, a moisture barrier tab or seal may be placed on across the second end 32 of the cap 14 to prevent activation of a desiccant placed therein. The tab may be removed prior to sealing the tube so the desiccant is activated and is still separated by the semi-permeable barrier or membrane of the second end 32.

The desiccant chamber 16 is configured to house the desiccant. The desiccant chamber may have dimensions determined by the type and amount of desiccant used to appropriately maintain desired humidity levels within the vessel 12 after a biological sample has been placed within and the cap 14 secured onto the vessel 12 to seal the contents. In one embodiment, for example, the desiccant chamber 16 may have an interior diameter of between 5-11 mm and may be between 6-13 mm in height. The desiccant chamber 16 may be configured to accept differing types and amounts of desiccant, for example, loose silica gel, silica gel packets, silica gel capsules, tablet desiccants, non-indicating silica gel, self-indicating silica gel, rice, montmorillonite clay, molecular sieve, calcium oxide, calcium sulfate, or other suitable desiccants.

Figure 6:
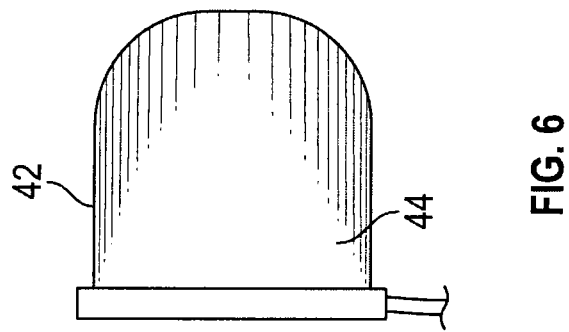
FIG. 6 is a side elevational view of a cap of the testing container of FIG. 5.
Figure 5:
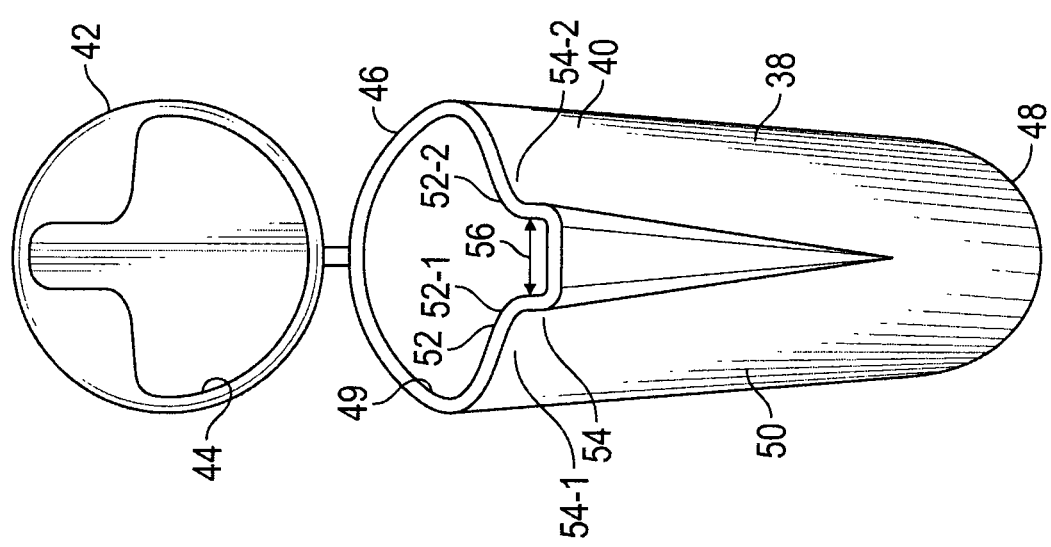
FIG. 5 is a perspective view of an embodiment of a testing container in accordance with the present disclosure.

Referring now to FIGS. 5 and 6, therein shown is another embodiment of a testing container 38. The testing container 38 includes a vessel 40, a cap 42, and a desiccant chamber 44 formed within the cap 42. The testing container 38 may be formed from materials similar to that of testing container 10 and formed by similar processes. For example, vessel 40 and the cap 42 may be formed via injection molding, 3D printing, or other processes. In some embodiments, the vessel 40 and the cap 42 are formed separate from one another such that the cap 42 and the desiccant chamber 44 may be secured to the vessel 40. In these embodiments, where the cap 42 and vessel 40 are formed separately, the cap 42 may be connected and secured to the vessel 40 via friction, a clip, a clamp, a locking mechanism, screw threads, or any other suitable mechanism.

The vessel 40 is provided with a first end 46, a second end 48 opposite the first end 46, and a sidewall 50 extending between the first end 46 and the second end 48. The first end 46 may form an opening 49 and the second end 48 may form a closed end. The sidewall 50 is provided with one or more protrusions 52 extending inwardly therefrom and formed from the sidewall 50. In the example shown, the sidewall 50 has a substantially constant thickness proximate to the opening 49, but is shaped to have one or more indentation 54 resulting in the one or more protrusions 52. As shown in FIG. 5, the vessel 40 is provided with a first protrusion 52-1 and a second protrusion 52-2 formed from a first indentation 54-1 and a second indentation 54-2, respectively. The first and second protrusion 52-1 and 52-2 may form a gap 56 extending therebetween approximately one third of a maximum internal diameter of the vessel 40. In some embodiments, the vessel 40 may be between 35-45 mm in height, and have an internal diameter of between 5-11 mm, for example. However, it will be understood that the dimensions of the vessel 40 may vary while still being insertable into a microfuge or liquid handling robot for automated processing. The first and second protrusions 52-1 and 52-2 may be used to break a shaft of a swab containing a sample, thereby removing a swab head from the swab, as previously discussed with regards to the testing container 10. The first and second indentations 54-1 and 54-2 may form a pitcher-like shape on an exterior of the sidewall 50 corresponding to the gap 56 within an interior of the sidewall 50 between the first and second protrusions 52-1 and 52-2. In some embodiments the gap 56 and the pitcher-like shape may taper between the first end 46 and the second end 48 of the vessel 40. In these embodiments, the sidewall 50 proximate to the second end 48 may be formed without the first and second indentations 54-1 and 54-2. In some embodiments, the gap 56 may be between 2-4 mm between the first and second protrusions 52-1 and 52-2. However, it should be understood that the gap 56 may be of varying dimensions based at least in part on dimensions of the vessel 40.

The cap 42 may be similar to the cap 14, with the exception that the cap 42 may interface with the opening 49 and the first and second indentations 54-1 and 54-2 of the vessel 40. In some embodiments, the cap 42 may connect to a rim 58 of the vessel 40 positioned at the first end 46. In other embodiments, the cap 42 may interface with at least a portion of the interior of the vessel 40 proximate to the first end 46, such as by a friction fit between a portion of the cap 42 inserted into the interior of the vessel 40 and the portion of the interior of the vessel 40. In some embodiments, the cap 42 may be provided without the desiccant chamber 44. In this embodiment, a semi-permeable membrane may allow air/moisture circulation between the testing container 38 and an environment outside of the testing container 38 while retaining a sample stored within the testing container 38 and preventing contamination of the sample. In other embodiments without the desiccant chamber 44, the cap 42 may be provided without the semi-permeable membrane to prevent communication between the testing container 38 and the environment outside of the testing container 38.

Figure 7:
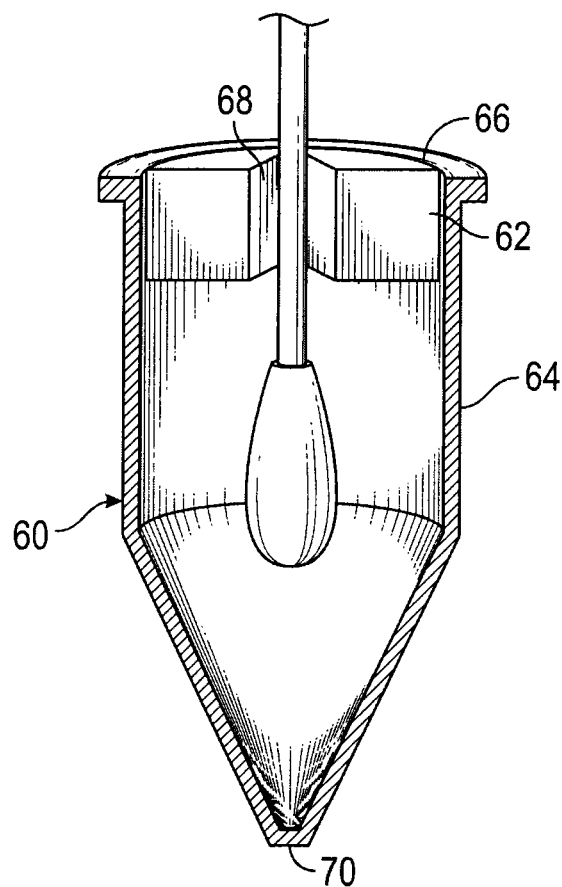
FIG. 7 is a partial side elevational view of an embodiment of a testing container in accordance with the present disclosure having a swab inserted into the testing container.
Figure 8:
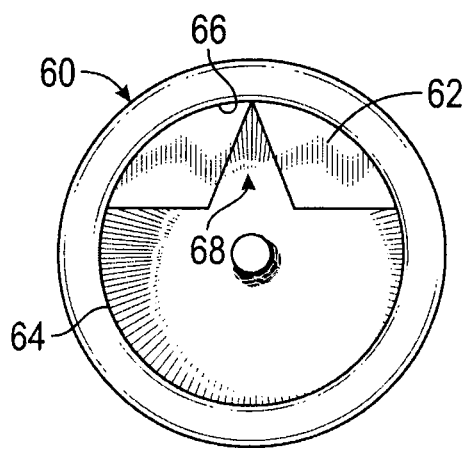
FIG. 8 is a partial top plan view of the testing container of FIG. 7.
Figure 9:
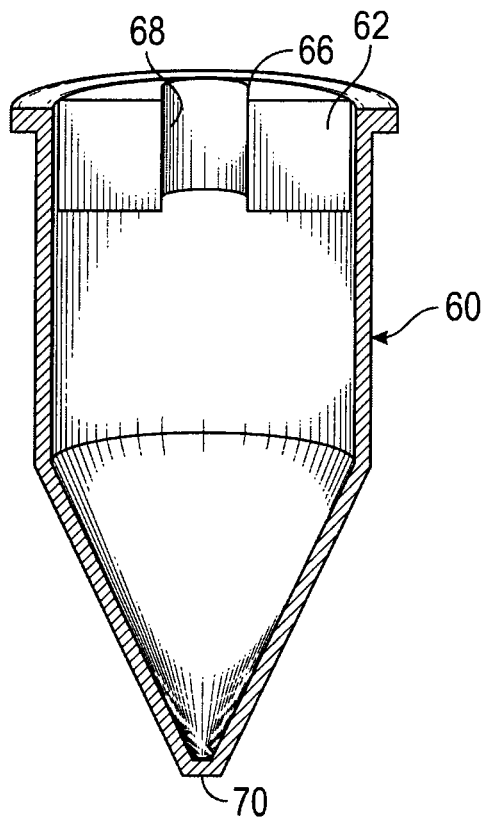
FIG. 9 is a partial side elevational view of an embodiment of a testing container in accordance with the present disclosure.
Figure 10:
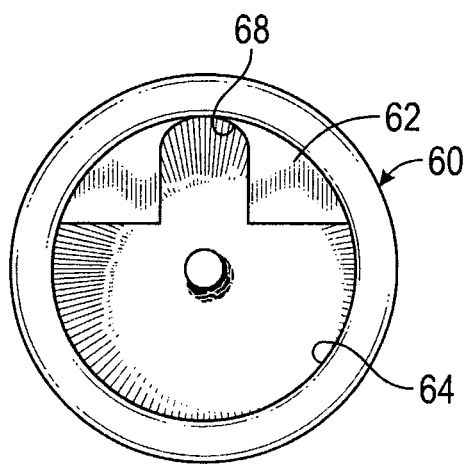
FIG. 10 is a partial top plan view of the testing container of FIG. 9.

Referring now to FIGS. 7-10, therein shown is another embodiment of a vessel 60 having a single protrusion 62 with a portion extending inwardly approximately one third of the internal diameter of the vessel 60. The single protrusion 62 extends from a sidewall 64 of the vessel 60 proximate to a first end 66 of the vessel 60. A gap 68 is shown extending into the single protrusion 62 at approximately the center of the single protrusion 62. The gap 68 may be triangular in shape (as shown in FIGS. 7 and 8), dome shaped (as shown in FIGS. 9 and 10), semi-circular, square, or any other suitable shape. In this embodiment, the single protrusion 62 extends proximate to the first end 66 of the vessel toward a second end 70 of the vessel 60 approximately 5-7 mm along the interior of the sidewall 64. It will be understood, however, that the single protrusion 62 may be of varying dimensions without departing from the function and the spirit of the inventive concepts of the present disclosure.

Referring now to FIGS. 11 and 12, another embodiment of a testing container 80 is shown. The testing container 80 is provided with a vessel 82, a cap 84, and a desiccant chamber 86. The testing container 80 may be implemented similarly to the testing container 10 with the exception that the vessel 82 may not include the one or more protrusions 26, as described above in relation to the vessel 12. In this embodiment, the vessel 82 of the testing container 80 may accept an insert vessel 88.

The insert vessel 88 has a first end 90, a second end 92, a sidewall 94 extending between the first end 90 and the second end 92, and one or more protrusion 96 extending inwardly from the sidewall 94 of the insert vessel 88. The first end 90 may form an opening in the insert vessel 88. The second end 92 may form a floor of the insert vessel 88. The second end 92 may be in the form of a mesh, a series of slots, or other suitable configuration allowing liquid, air, and particles below a predetermined size to pass through the second end 92 while preventing larger particles and solids from passing through and leaving the insert vessel 88. The second end 92, being permeable to air and liquid may allow a sample fluid to pass into the vessel 82 through the insert vessel 88, when inserted into the testing container 80. The insert vessel 88 may be formed from polyethylene, polyallomer, polypropylene, glass, or other suitable materials. In one embodiment, the insert vessel 88 may be formed using, for example, injection molding. The insert vessel 88 may have an exterior diameter of between 5-11 mm, and may have a height of between 15-20 mm measured from the first end 90 to the second end 92. Insert vessel 88 may be secured into testing vessel 80 by a friction fit or locking mechanism.

The one or more protrusion 96 may be implemented similarly to the one or more protrusion 26, the first and second protrusions 26-1 and 26-2, or the single protrusion 62. In another embodiment, as shown in FIG. 12, the one or more protrusion 96 may be formed as a first protrusion 98-1 and a second protrusion 98-2 formed on opposing sides of the insert vessel 88 and extending inwardly toward the center of the insert vessel 88. A first gap 100-1 and a second gap 100-2 may be formed within the first protrusion 98-1 and the second protrusion 98-2, respectively. In one embodiment, the first and second protrusions 98-1 and 98-2 may extend into the insert vessel 88 approximately one third of the internal diameter.

Figure 13:
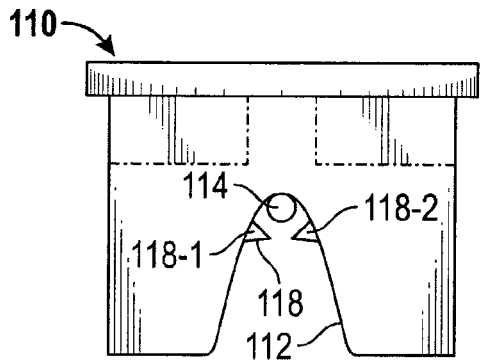
FIG. 13 is a side elevational view of an embodiment of an insert vessel in accordance with the present disclosure.
Figure 14:
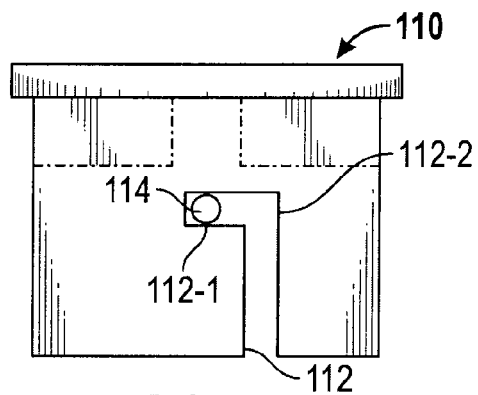
FIG. 14 is a side elevational view of another embodiment of the insert vessel of FIG. 13.

Referring now to FIGS. 13 and 14, another embodiment of an insert vessel 110 is shown. The insert vessel 110 may be implemented similarly to the insert vessel 88 with the exception that the insert vessel 110 has a receiving slot 112 configured to receive a locking protrusion 114 of a testing container (not shown). In some embodiments, the receiving slot 112 may be provided with one or more locking tabs 118. As shown in FIG. 13, the insert vessel 110 is provided with a two locking tabs 118-1 and 118-2 cooperating to receive the locking protrusion 114 extending inwardly from an interior of the testing container. Once the locking protrusion 114 is accepted into the receiving slot 112 and passes the two locking tabs 118-1 and 118-2, the locking protrusion 114, the receiving slot 112, and the two locking tabs 118-1 and 118-2 cooperate to secure the insert vessel 110 within the testing container. In another embodiment, as shown in FIG. 14, the insert vessel 110 is configured to receive the locking protrusion 114 and secure the insert vessel 110 within the testing container without the one or more locking tabs 118. As shown in FIG. 14, the receiving slot 112 is provided with a first portion 112-1 substantially perpendicular to a second portion 112-2 of the receiving slot 112. However, it will be understood that the receiving slot 112 may be configured with the first portion 112-1 and the second portion 112-2 positioned at any angle with respect to one another that will function to secure the insert vessel 110 within the testing container. In some embodiments, the insert vessel 110 may be frustoconical, cylindrical, or other shapes configured to correspond to a shape of the testing container.

Figure 15:
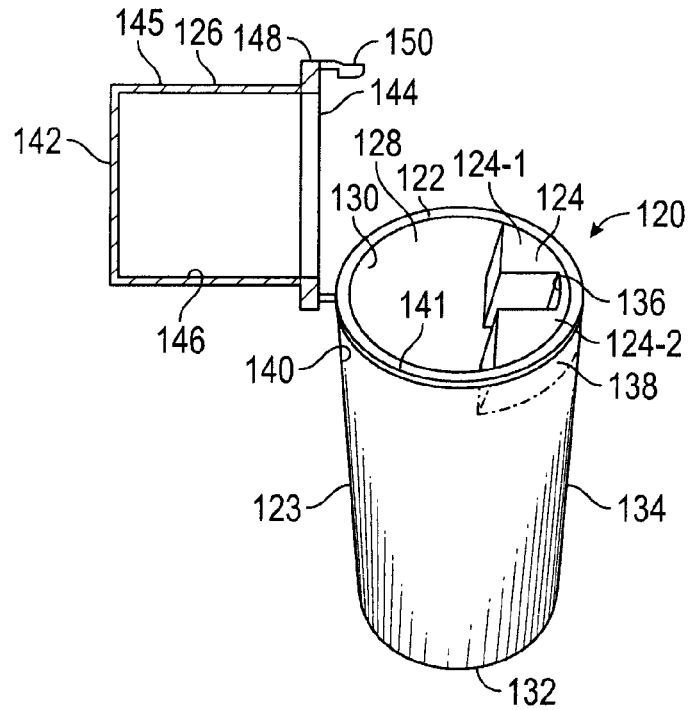
FIG. 15 is a perspective view of a testing container and an insert in accordance with the present disclosure.

Referring now to FIG. 15, another embodiment of an insert 120 is shown. In one embodiment, the insert 120 may be provided with an engagement member 122 configured to at least partially surround and engage a testing container 123 proximate to an opening of the testing container 123, one or more protrusions 124 extending inwardly from the engagement member 122, and a cap 126 connected to the engagement member 122. The testing container 123, similar to the testing containers 10 and 80, may have a first end 128 forming an opening 130, a second end 132, and a sidewall 134 extending between the first and second ends 128 and 132. The insert 120 may be formed from polyethylene, polyallomer, polypropylene, glass, or other suitable materials. In one embodiment, the insert 120 may be formed using, for example, injection molding or 3D printing, and may be formed such that the engagement member 122, the one or more protrusions 124, and the cap 126 are of a single piece construction. In another embodiment, the engagement member 122 and the one or more protrusion 124 may be formed separately from the cap 126 such that the cap 126 may be secured to the engagement member 122. The insert 120 may be configured to be at least partially inserted and/or connected to the testing container 123, where the testing container 123, similar to testing containers 10 and 80, is configured to a standard size of a microfuge tube such that the testing container 123 may be inserted within a microfuge or liquid handling robot for automated processing.

The engagement member 122, as shown in FIG. 15, may be substantially ring shaped and configured to engage the testing container 123 proximate to the opening 130 of the testing container 123. In embodiments where the testing container 123 is non-circular, the engagement member 122 may be shaped to correspond to the testing container 123. The engagement member 122 may have a sidewall 135 configured to contact at least a portion of the testing container 123 and extend a distance between the first end 128 and the second end 132 of the testing container along the sidewall 134. The engagement member 122 may engage the testing container 123 via latch, screw threads, a lip, a clip, a clamp, a friction fit, a locking mechanism, or any other suitable mechanism. In some embodiments, the engagement member 122 may engage the first end 128 of the testing container 123, such as by friction fit extending contacting a portion of an interior or exterior surface of the sidewall 134 of the testing container 123, for example. In some embodiments, the engagement member 122 may engage an outer rim of the testing container 123 proximate to the first end 128, such as by a lip fitting around an exterior of the outer rim and engaging an underside of the outer rim, for example. In other embodiments, the engagement member 122 may be configured to engage the exterior of the testing container 123, while the one or more protrusion 124 contacts the interior of the testing container 123. While in still other embodiments, the engagement member 122 is configured to engage the testing container 123 using a receiving slot and locking protrusion similar to that of the insert vessel 110. In either event, when the engagement member 122 engages the testing container 123, the one or more protrusion 124 may be positioned within the interior of the testing container 123 and extend at least partially between the first and second ends 128 and 132 along the sidewall 134.

The one or more protrusion 124 may be formed from polyethylene, polyallomer, polypropylene, glass, or other suitable materials and formed through the same process as the insert 120, such that the one or more protrusion 124 form a part of the insert 120. The one or more protrusion 124 may also be formed independent of the insert 120 and connected thereto such that the one or more protrusion 124 extends inwardly from the engagement member 122 of the insert 120. As shown in FIG. 15, the one or more protrusion 124 may be provided as a first protrusion 124-1 and a second protrusion 124-2, extending inwardly approximately one third of the internal diameter of the insert 120. The first and second protrusions 124-1 and 124-2 may form a gap 136 therebetween, having a width extending approximately one third of an internal diameter of the insert 120 between the first and second protrusions 124-1 and 124-2. It will be understood that the one or more protrusion 124 and the gap 136 may be of varying dimensions so long as the one or more protrusions 124 may be inserted into the testing container 123 and may aid the user to break the shaft of the swab and/or otherwise remove the head of the swab, as described above and below.

The one or more protrusion 124 may have an outer surface 138 that is aligned with at least a portion of the engagement member 122. The outer surface 138 may be shaped so as to mate with an interior surface 140 of the testing container 123. For example, where the testing container 123 is cylindrical, the outer surface 138 may form an arc shape. Further, by way of example, where the testing container 123 has a substantially square cross section, the outer surface 138 of the one or more protrusion 124 may form a flat portion or a plurality of flat portions to mate with one or more portion of the interior surface 140. The one or more protrusion 124 may be of varying lengths extending downwardly from the engagement member 122. In one embodiment, the one or more protrusion 124 may extend downwardly from a first end 141 of the engagement member 122 without extending downwardly beyond the sidewall 135 of the engagement member 122. When the insert 120 is connected to the testing container 123 and the one or more protrusions 124 inserted therein, the one or more protrusions 124 may extend between the first and second ends 128 and 132 of the testing container 123 along the interior surface 140 and, in some embodiments, may contact the interior surface 140. For example, in one embodiment, where the testing container 123 is between 35-45 mm in height, the one or more protrusions 124 may extend between 5-7 mm along the interior surface 140 of the sidewall 134 of the testing container 123.

Figure 16:
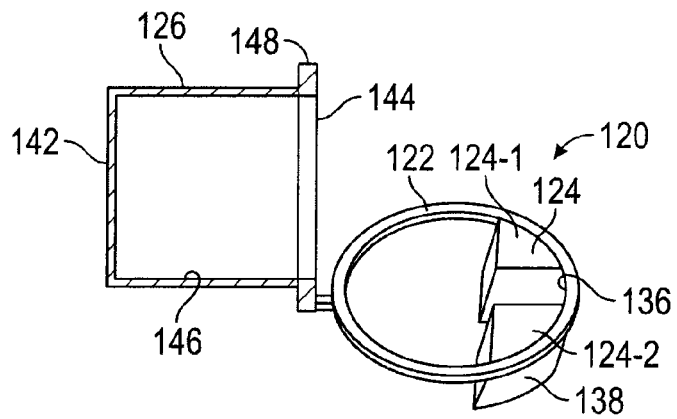
FIG. 16 is a perspective view of another embodiment of the insert of FIG. 15 in accordance with the present disclosure.

The gap 136, formed by the first and second protrusions 124-1 and 124-2 may be formed in a substantially rectangular shape, as shown in FIGS. 15 and 16. In other embodiments, the gap 136 may extend into a single protrusion of the one or more protrusions 124, similar to the gap 68, described above. The gap 136 may be triangular in shape, dome shaped, semicircular, square, polygonal, or any other suitable shape. As shown, the gap 136, in one embodiment, may be sized proportionally to the testing container 123, such that the gap has a width extending approximately one third of the internal diameter of the testing container 123 and the insert 120. For example, where the testing container has an internal diameter of between 5-11 mm, the gap 136 may have a width of between 2-4 mm. In other embodiments, as previously stated, the gap 136 may have a width greater than or less than the one third of the internal diameter of the testing container 123 and the insert 120.

The cap 126 may be implemented similarly to the caps 14 or 84, with a first end 142, a second end 144, and a sidewall 145 extending between the first end 142 and the second end 144. However the cap 126 differs from the caps 14 and 84 in that the cap 126 is configured to engage the engagement member 122 of the insert 120, proximate to a second end 144 of the cap 126, to secure the cap 126 to the insert 120. In some embodiments, the cap 126 may have a circular, triangular, square, polygonal, or other suitable shaped cross section and have a generally cylindrical shape, dome shape, frustoconical shape, or any other suitable shape extending vertically from the engagement member 122, when secured thereto. The cap 126 may be provided with a desiccant chamber 146 extending between the first end 142 and the second end 144, where the first end 142 forms a top of the desiccant chamber 146 and the second end 144 forms a bottom of the desiccant chamber 146. The second end 144 may be a semi-permeable membrane, similar to one described embodiment of the cap 14. The cap 126, in one embodiment, may have a substantially constant thickness such that a shape of the desiccant chamber 146 corresponds to a shape of the cap 126. In some embodiments, the cap 126 may be provided without the desiccant chamber 146. In this embodiment, the semi-permeable membrane may allow air/moisture circulation between the testing container 123 and an environment outside of the testing container 123 while retaining a sample stored within the testing container 123 and preventing contamination of the sample. In other embodiments without the desiccant chamber 146, the cap 42 may be provided without the semi-permeable membrane to prevent communication between the testing container 123 and the environment outside of the testing container 123.

The cap 126 may further be provided with a rim 148 extending outwardly from the cap 126 proximate to the second end 144. In some embodiments, the cap 126 may secure to the engagement member 122 or the testing container 123 via a latch 150 capable of interfacing with the engagement member 122 or the outer rim of the testing container 123. In one embodiment, as shown, the latch 150 may be connected to the rim 148 and extend outwardly from the second end 144 such that the latch 150, when in the closed position, is at least partially aligned with the engagement member 122 and the one or more protrusion 124. The cap 126, in other embodiments, may also secure to the engagement member 122 via friction fit, a clip, a clamp, a locking mechanism, or any other suitable mechanism. In some embodiments, as shown in FIG. 16, the cap 126 may secure to the engagement member via the rim 148. For example, the rim 148 may extend outwardly from the cap 126 a distance and downwardly past the second end 144 of the cap 126, such that the rim 148 may engage the engagement member 122 by friction fit around a circumference of the engagement member 122. In some embodiments, the rim 148 may also engage the engagement member 122 by a latch, locking mechanism, screw threads, a lip, or any other suitable mechanism. When the insert 120 is inserted into the testing container 123 and the cap 126 secured to the engagement member 122, the cap 126 may thereby secure to the testing container 123. In one embodiment, when secured to the testing container 123, the cap 126 may allow air and moisture circulation between the testing container and the desiccant chamber 130 of the cap 126.

The second end 144, where implemented as the semi-permeable membrane, may be configured to permit air passage between the desiccant chamber 146 and the testing container 123 when the insert 120 is secured to the testing container 123. The semi-permeable membrane may be implemented as a paper, a polymeric material in a mesh configuration, a polymeric material in a slotted configuration, or any other suitable material or configuration which may prevent a desiccant stored within the desiccant chamber 146 from contacting contents of the testing container 123 or entering the testing container 123.

In use, the testing container 10 may be sealed in a package, such as a plastic bag, foil bag, or other suitable container to prevent activation of the desiccant within the desiccant chamber 16. A user may obtain the testing container 10 and remove it from the sealed package. The user may use a swab, with a wooden or plastic shaft, to obtain a biological sample such as blood, saliva, and cellular samples, for example. The user may then place the tip of the swab, used to collect the sample, into the vessel 12 of the testing container 10. In the embodiment shown in FIG. 1, the shaft of the swab may then be placed between the first and second protrusions 26-1 and 26-2. Lateral pressure may then be applied to the shaft breaking the shaft between the first and second protrusions 26-1 and 26-2. When the shaft breaks, the tip of the swab (also referred to herein as the head of the swab) containing the biological sample, may fall into the vessel 12. The cap 14 of the testing container 10 may be closed, sealing the vessel 12 from outside contaminants and moisture. The desiccant within the desiccant chamber 16, activated by removing the testing container 10 from the sealed package or removing the barrier tab, may absorb the moisture from the air within the vessel 12, drying the biological sample to preserve the biological sample for later testing. The testing container 10, with the contents of the vessel 12 sealed by the cap 14 may be transported to a location for testing, such as a mobile or stationary lab, or other testing facility, for example. The testing container 10 may also be stored in an evidence containment unit, such as an evidence locker in a police station, prior to testing. For testing the biological sample, the testing container 10 may be opened, and placed in a rack of an automated processing instrument for processing. Otherwise, the biological sample may be rehydrated using an appropriate solution, such as 1 ml lysis buffer and 10 µl Proteinase K, or other suitable solution and processed manually. It will be understood by one skilled in the art that other forms of testing of the biological sample may be performed while the biological sample remains in the testing container 10.

The testing container 80 may be used similar to the testing container 10. The testing container 80 may be sealed in a suitable container to prevent activation of the desiccant in the desiccant chamber 86 (or have a barrier tab). The insert vessel 88 may be packaged with the testing container 80, or may be separate from the testing container 80. A user may obtain the testing container 80 and remove it from the sealed package. The user may then insert the insert vessel 88 into the testing container 80 such that the insert vessel 88 is secured within the vessel 82 of the testing container 80. The user may use a swab, with a wooden or plastic shaft, for example, to obtain a biological sample such as blood, saliva, and cellular samples, for example. The user may then place the tip of the swab, used to collect the sample, into the insert vessel 88 within the testing container 80. In the embodiment shown in FIG. 11, the shaft of the swab may then be placed between the first and second protrusions 98-1 and 98-2. Lateral pressure may then be applied to the shaft breaking the shaft between the first and second protrusions 98-1 and 98-2. When the shaft breaks, the tip of the swab, containing the biological sample, may fall into the insert vessel 88. The cap 84 of the testing container 80 may be closed, sealing the vessel 82 from outside contaminants and moisture. The desiccant within the desiccant chamber 86, activated by removing the testing container 80 from the sealed package (or removing barrier tab), may absorb the moisture from the air within the vessel 82, drying the biological sample to preserve the biological sample for later testing. The testing container 80, with the contents of the vessel 82 sealed by the cap 84 may be transported to a location for testing, such as a mobile or stationary lab, or other testing facility, for example. The testing container 80 may also be stored in an evidence containment unit, such as an evidence locker in a police station, prior to testing. For testing the biological sample, the testing container 80 may be opened, and if necessary, the biological sample may be rehydrated using an appropriate solution, such as 1 ml lysis buffer and 10 µl Proteinase K, or other suitable solution. When the appropriate solution is applied to the biological sample, the sample and solution may pass through the second end 92 of the insert vessel 88 and enter into the vessel 82 of the testing container 80. The insert vessel 88 may then be removed from the testing container 80 in order to remove the swab tip and the testing container 80 may be placed into a microfuge or liquid handling robot for automated processing for separation of the biological sample and later analysis. It will be understood by one skilled in the art that other forms of testing of the biological sample may be performed while the biological sample remains in the testing container 80.

What is claimed is:
1. A testing container, comprising:
   a vessel having a first end, a second end, and a sidewall extending between the first end and the second end, the first end forming an opening into the vessel, and at least two protrusions positioned directly adjacent to the first end and extending inwardly relative to the sidewall, the at least two protrusions being aligned, in a side-by-side relationship and forming a gap with edges in opposed relationship having a width in a range between 2-4 mm, the at least two protrusions configured to provide sufficient strength to withstand lateral pressure applied to a shaft of a swab positioned in the gap in order to break the shaft of the swab while leaving a head of the swab attached to a portion of the shaft such that the head and the portion of the shaft connected to the head falls into the vessel.

2. The testing container of claim 1, further comprising a cap having a first end, a second end, and a desiccant chamber, the cap configured to seal the opening of the vessel, the desiccant chamber configured to house a desiccant and wherein the second end of the cap has a semi-permeable barrier configured to allow air and moisture circulation between the vessel and the desiccant chamber.

3. The testing container of claim 2 further comprising a desiccant positioned within the desiccant chamber.

4. A testing container, comprising:
a vessel having a first end, a second end, and a sidewall extending between the first end and the second end, the first end forming an opening into the vessel, the second end forming a closed end of the vessel opposite the opening;
an insert vessel positioned in the vessel, the insert vessel having a first end, a second end, and a sidewall, the first end forming an opening into the insert vessel and the sidewall having at least two protrusions positioned directly adjacent to the first end and extending inwardly relative to the sidewall, the at least two protrusions being aligned, in a side-by-side relationship and forming a gap with edges in opposed relationship having a width in a range between 2-4 mm, the at least two protrusions configured to provide sufficient strength to withstand lateral pressure applied to a shaft of a swab positioned in the gap in order to break the shaft of the swab while leaving a head of the swab attached to a portion of the shaft such that the head and the portion of the shaft connected to the head falls into the vessel;
a cap having a first end, a second end, and a desiccant chamber, the cap configured to secure the opening of the vessel, the second end of the cap having a semi-permeable barrier configured to allow air and moisture circulation between the vessel and the desiccant chamber, and a moisture barrier tab extending across the semi-permeable barrier to seal the desiccant chamber, the moisture barrier tab being removably attached to the cap; and
a desiccant positioned in the desiccant chamber.

5. The testing container of claim 4, wherein the second end of said cap forms a floor of the cap.

6. The testing container of claim 5, wherein the second end of said cap is permeable to a sample fluid.

7. The testing container of claim 6, wherein the second end of said cap forms a mesh configured to allow liquid, air, and particles below a predetermined size to pass through the second end while preventing larger particles from passing through the cap.

8. The testing container of claim 6, wherein the second end of said cap forms a series of slots configured to allow liquid, air, and particles below a predetermined size to pass through the second end while preventing larger particles from passing through the cap.

9. An insert vessel, comprising:
a vessel configured to be accepted into a testing container, having a first end, a second end, and a sidewall extending between the first end and the second end, the first end forming an opening into the vessel and the sidewall having at least two protrusions positioned directly adjacent to the first end and extending inwardly relative to the sidewall, the at least two protrusions being aligned, in a side-by-side relationship and forming a gap with edges in opposed relationship having a width in a range between 2-4 mm, the at least two protrusions configured to provide sufficient strength to withstand lateral pressure applied to a shaft of a swab positioned in the gap in order to break the shaft of the swab while leaving a head of the swab attached to a portion of the shaft such that the head and the portion of the shaft connected to the head falls into the vessel, and wherein the vessel is configured to be inserted into a testing container.

10. The insert vessel of claim 9, wherein the second end forms a floor of the insert vessel.

11. The insert vessel of claim 10, wherein the second end is permeable to a sample fluid.

12. The insert vessel of claim 11, wherein the second end forms a mesh configured to allow liquid, air, and particles below a predetermined size to pass through the second end while preventing larger particles from passing through the vessel.

13. The insert vessel of claim 11, wherein the second end forms a series of slots configured to allow liquid, air, and particles below a predetermined size to pass through the second end while preventing larger particles from passing through the vessel.

14. A testing container, comprising:
a vessel having a first end, a second end, and a sidewall extending between the first end and the second end, the first end forming an opening into the vessel, the second end forming a closed end of the vessel, the vessel further comprising at least two protrusions positioned directly adjacent to the first end and extending inwardly relative to the sidewall, the at least two protrusions being aligned, in a side-by-side relationship and forming a gap with edges in opposed relationship having a width in a range between 2-4 mm, the at least two protrusions configured to provide sufficient strength to withstand lateral pressure applied to a shaft of a swab positioned in the gap in order to break the shaft of the swab while leaving a head of the swab attached to a portion of the shaft such that the head and the portion of the shaft connected to the head falls into the vessel;
a desiccant;
a cap having a first end, a second end, and a desiccant chamber, the cap configured to secure the opening of the vessel, the cap supporting the desiccant in the desiccant chamber so as to allow air and moisture circulation between the vessel and the desiccant; and
a moisture barrier tab extending across the semi-permeable barrier to seal the desiccant chamber, the moisture barrier tab being removably attached to the cap.

15. The testing container of claim 1, wherein the at least two protrusions is a single structure having the gap separating a first portion and a second portion of the single structure, the first portion being a first protrusion of the at least two protrusions, and the second portion being a second protrusion of the at least two protrusions with the first portion and the second portion aligned, in the side-by-side relationship and with edges of the first portion and the second portion in opposed relationship.

16. The testing container of claim 4, wherein the at least two protrusions is a single structure having the gap separating a first portion and a second portion of the single structure, the first portion being a first protrusion of the at least two protrusions, and the second portion being a second protrusion of the at least two protrusions with the first portion and the second portion aligned, in the side-by-side relationship and with edges of the first portion and the second portion in opposed relationship.

17. The insert vessel of claim 6, wherein the at least two protrusions is a single structure having the gap separating a first portion and a second portion of the single structure, the first portion being a first protrusion of the at least two protrusions, and the second portion being a second protrusion of the at least two protrusions with the first portion and the second portion aligned, in the side-by-side relationship and with edges of the first portion and the second portion in opposed relationship.

18. The testing container of claim 14, wherein the at least two protrusions is a single structure having the gap separating a first portion and a second portion of the single structure, the first portion being a first protrusion of the at least two protrusions, and the second portion being a second protrusion of the at least two protrusions with the first portion and the second portion aligned, in the side-by-side relationship and with edges of the first portion and the second portion in opposed relationship.

* * * * *

UNITED STATES PATENT AND TRADEMARK OFFICE
CERTIFICATE OF CORRECTION

| | | |
|---|---|---|
| PATENT NO. | : 9,103,749 B2 | Page 1 of 1 |
| APPLICATION NO. | : 13/965987 | |
| DATED | : August 11, 2015 | |
| INVENTOR(S) | : Randolph J. Nagy | |

It is certified that error appears in the above-identified patent and that said Letters Patent is hereby corrected as shown below:

In The Claims:
Column 15, line 4: Delete "claim 6," and replace with -- claim 9, --

Signed and Sealed this
Fifteenth Day of December, 2015

Michelle K. Lee
*Director of the United States Patent and Trademark Office*